(12) United States Patent
Nakagawa (10) Patent No.: US 10,470,642 B2
(45) Date of Patent: Nov. 12, 2019

(54) OPTICAL TRANSMITTER AND ENDOSCOPE

(71) Applicant: OLYMPUS CORPORATION, Tokyo (JP)

(72) Inventor: Yusuke Nakagawa, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/100,391

(22) Filed: Aug. 10, 2018

(65) Prior Publication Data

US 2018/0368659 A1    Dec. 27, 2018

Related U.S. Application Data

(63) Continuation of application No. PCT/JP2016/054537, filed on Feb. 17, 2016.

(51) Int. Cl.
*A61B 1/00* (2006.01)
*A61B 1/05* (2006.01)
(Continued)

(52) U.S. Cl.
CPC ...... *A61B 1/00009* (2013.01); *A61B 1/00006* (2013.01); *A61B 1/00013* (2013.01);
(Continued)

(58) Field of Classification Search
CPC ............ A61B 1/00009; A61B 1/00006; A61B 1/00013; A61B 1/00096; A61B 1/00117;
(Continued)

(56) References Cited

U.S. PATENT DOCUMENTS 6,517,259 B1    2/2003  Murata
6,917,745 B2 *  7/2005  Murata ................. B29D 11/00
                                             385/137
(Continued)

FOREIGN PATENT DOCUMENTS

EP       1061391 A2    12/2000
JP    2001059924 A     3/2001
(Continued)

OTHER PUBLICATIONS

International Search Report dated May 24, 2016 issued in PCT/JP2016/054537.

*Primary Examiner* — Dalzid E Singh
(74) *Attorney, Agent, or Firm* — Scully, Scott, Murphy & Presser, P.C.

(57) ABSTRACT

An optical transmitter includes an optical device, a wiring board including a first main surface and a second main surface, the optical device being mounted at a position closer to the second main surface than to the first main surface, a holding member fixed to the wiring board, at a position closer to the first main surface than to the second main surface, and an optical fiber inserted into a through hole of the holding member, where the wiring board includes a wiring pattern of a wiring layer sandwiched between an upper insulating layer and a lower insulating layer, and further includes an opening from which an upper surface and a lower surface of the wiring pattern are exposed, and an end surface of the optical fiber is in contact with the upper surface, and an external electrode of the optical device is bonded to the lower surface.

10 Claims, 8 Drawing Sheets

(51) Int. Cl.
*G02B 6/42* (2006.01)
*G02B 23/24* (2006.01)
*A61B 1/06* (2006.01)

(52) U.S. Cl.
CPC ...... *A61B 1/00096* (2013.01); *A61B 1/00117* (2013.01); *A61B 1/00165* (2013.01); *A61B 1/051* (2013.01); *G02B 6/4281* (2013.01); *G02B 23/24* (2013.01); *A61B 1/05* (2013.01); *A61B 1/0676* (2013.01); *G02B 6/4231* (2013.01); *G02B 6/4292* (2013.01)

(58) Field of Classification Search
CPC ....... A61B 1/00165; A61B 1/051; A61B 1/05; A61B 1/0676; G02B 6/4281; G02B 6/4231; G02B 6/4292; G02B 23/24
USPC ......................................................... 398/182
See application file for complete search history.

(56) References Cited

U.S. PATENT DOCUMENTS

| | | | |
|---|---|---|---|
| 8,705,906 B2* | 4/2014 | Im | G02B 6/4201 |
| | | | 385/14 |
| 2007/0286231 A1* | 12/2007 | Kubo | A61B 1/00006 |
| | | | 370/464 |
| 2015/0086162 A1* | 3/2015 | Miyahara | G02B 23/2423 |
| | | | 385/33 |
| 2015/0098237 A1 | 4/2015 | Motohara | |

FOREIGN PATENT DOCUMENTS

| | | |
|---|---|---|
| JP | 2004354532 A | 12/2004 |
| JP | 2014010329 A | 1/2014 |
| WO | 2014002616 A1 | 1/2014 |

\* cited by examiner

OPTICAL TRANSMITTER AND ENDOSCOPE

CROSS REFERENCE TO RELATED APPLICATION

This application is a continuation application of PCT/JP2016/054537 filed on Feb. 17, 2016, the entire contents of which are incorporated herein by this reference.

BACKGROUND OF INVENTION

1. Field of the Invention

The present invention relates to an optical transmitter including an optical device, a wiring board including a first main surface and a second main surface facing the first main surface, and on which the optical device is mounted, a holding member fixed to the wiring board, and including a through hole perpendicular to the first main surface, and an optical fiber inserted into the through hole of the holding member, and to an endoscope including the optical transmitter.

2. Description of the Related Art

An endoscope includes, at a distal end portion of an elongated insertion portion, an image pickup unit including an image pickup device such as a CCD. In recent years, use of an image pickup device with a large number of pixels is being considered with respect to endoscopes. In a case of using an image pickup device with a large number of pixels, an amount of signal transmitted from the image pickup device to a signal processing apparatus is increased, and thus, optical signal transmission through an optical fiber using an optical signal is preferably used instead of electric signal transmission through metal wiring using an electric signal. For optical signal transmission, an E/O optical transmitter (electro-optical converter) configured to convert an electric signal into an optical signal, and an O/E optical transmitter (opto-electrical converter) configured to convert the optical signal into the electric signal are used.

With the optical transmitter, an optical coupling efficiency between an optical device and an optical fiber is important. To increase the optical coupling efficiency, a distance between the optical device and an end surface of the optical fiber is desirably reduced.

Japanese Patent Application Laid-Open Publication No. 2004-354532 discloses an optical transmitter configured to enable insertion/removal of an optical fiber. With the optical transmitter, the optical device is connected to a wire (flying lead) exposed from a hole (opening portion) of a wiring board. The optical fiber is configured to be capable of being inserted/removed with respect to the hole of the wiring board.

With the optical transmitter, accurate positioning has to be performed with respect to relative positions of the optical device and a holding portion (ferrule) where the optical fiber is inserted. That is, if a center position of a light emitting portion of the optical device and a center position of a through hole of the holding portion are shifted from each other, amount of light entering the optical fiber is reduced, and a signal is attenuated, for example.

To reduce a burden on a subject, and to secure an observation field of view, an outer diameter and a length of a distal end portion of an insertion portion of an endoscope are desirably reduced as much as possible. An optical transmitter for endoscope is thus much smaller than an optical transmitter for general communications. Accordingly, the optical device and the optical fiber require particularly accurate positioning.

SUMMARY OF THE INVENTION

An optical transmitter according to an aspect of the present invention is an optical transmitter including an optical device including a light emitting portion configured to output light of an optical signal or a light receiving portion to which light of an optical signal is inputted; a wiring board including a first main surface and a second main surface facing the first main surface, the optical device being mounted at a position closer to the second main surface than to the first main surface; a holding member fixed to the wiring board, at a position closer to the first main surface than to the second main surface, the holding member including a through hole perpendicular to the first main surface; and an optical fiber inserted into the through hole of the holding member, and configured to transmit the optical signal, where the wiring board includes a wiring pattern with a flat plate shape on a wiring layer sandwiched between an upper insulating layer and a lower insulating layer, and further includes an opening penetrating through the upper insulating layer and the lower insulating layer, and from which an upper surface and a lower surface of the wiring pattern are exposed, and an end surface of the optical fiber is in contact with the upper surface of the wiring pattern, and an external electrode of the optical device is bonded to the lower surface.

An endoscope according to another aspect includes, at a rigid distal end portion of an insertion portion, an optical transmitter including an optical device including a light emitting portion configured to output light of an optical signal or a light receiving portion to which light of an optical signal is inputted; a wiring board including a first main surface and a second main surface facing the first main surface, the optical device being mounted at a position closer to the second main surface than to the first main surface; a holding member fixed to the wiring board, at a position closer to the first main surface than to the second main surface, the holding member including a through hole perpendicular to the first main surface; and an optical fiber inserted into the through hole of the holding member, and configured to transmit the optical signal, where the wiring board includes a wiring pattern with a flat plate shape on a wiring layer sandwiched between an upper insulating layer and a lower insulating layer, and further includes an opening penetrating through the upper insulating layer and the lower insulating layer, and from which an upper surface and a lower surface of the wiring pattern are exposed, and an end surface of the optical fiber is in contact with the upper surface of the wiring pattern, and an external electrode of the optical device is bonded to the lower surface.

DETAILED DESCRIPTION OF THE PREFERRED EMBODIMENTS

First Embodiment

Figure 1:
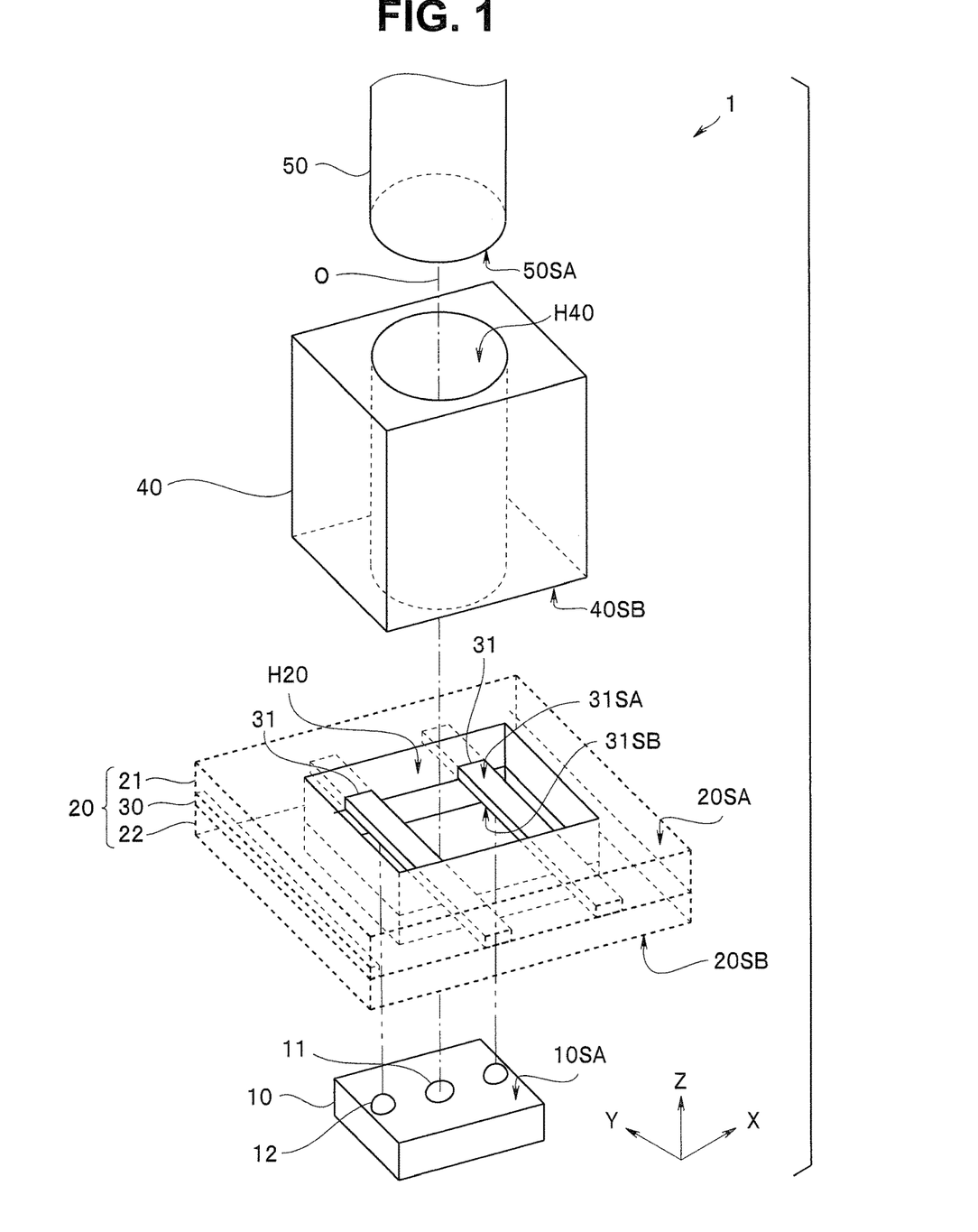
FIG. 1 is an exploded view of an optical transmitter according to a first embodiment.

An optical transmitter 1 according to a first embodiment will be described with reference to FIGS. 1 to 3. Note that in the following description, drawings of respective embodiments are schematic, and the relationship between a thickness and a width of each member, the ratio of thicknesses of respective members, and the like are not actual, and the relationship between dimensions and the ratios may be different between the drawings. Illustration of some components, and use of reference signs may be omitted. A direction in which an optical fiber 50 is disposed (i.e., an increasing direction on a Z-axis) is referred to as "top".

The optical transmitter 1 according to the present embodiment is an E/O module configured to convert an electric signal into an optical signal, and to transmit the optical signal.

The optical transmitter 1 includes an optical device 10 including a light emitting portion 11 configured to output light of an optical signal, a wiring board 20, a holding member (ferrule) 40, and an optical fiber 50 configured to transmit the optical signal.

The wiring board 20 includes a first main surface 20SA positioned at a top, and a second main surface 20SB facing the first main surface 20SA, and the optical device 10 is mounted in a downward direction, or in other words, at a position closer to the second main surface 20SB than to the first main surface 20SA. The holding member 40 is fixed in an upward direction of the wiring board 20, or in other words, at a position closer to the first main surface SA than to the second main surface 20SB, and includes a through hole H40 perpendicular to the first main surface 20SA (second main surface 20SB). A distal end portion of the optical fiber 50 is inserted and fixed in the through hole H40 of the holding member 40.

The wiring board 20 includes a flat plate-shaped wiring pattern 31 on a wiring layer 30 sandwiched between an upper insulating layer 21 and a lower insulating layer 22. The wiring board 20 includes an opening H20 penetrating through the upper insulating layer 21 and the lower insulating layer 22, and from which an upper surface 31SA and a lower surface 31SB of the wiring pattern 31 are exposed.

An end surface 50SA of the optical fiber 50 is in contact with the upper surface 31SA of the wiring pattern 31, and an external electrode 12 of the optical device 10 is bonded to the lower surface 31SB. The lower surface 31SB is closer to the second main surface 20SB than to the first main surface 20SA.

Figure 2:
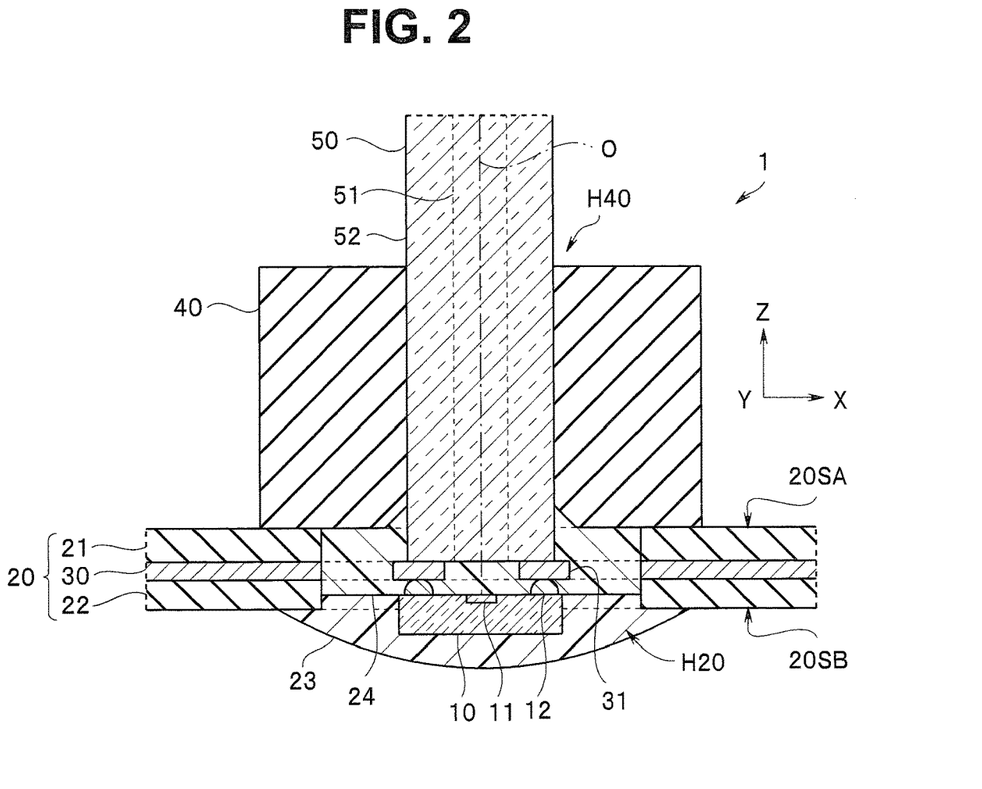
FIG. 2 is a cross-sectional view of the optical transmitter according to the first embodiment.
Figure 3:
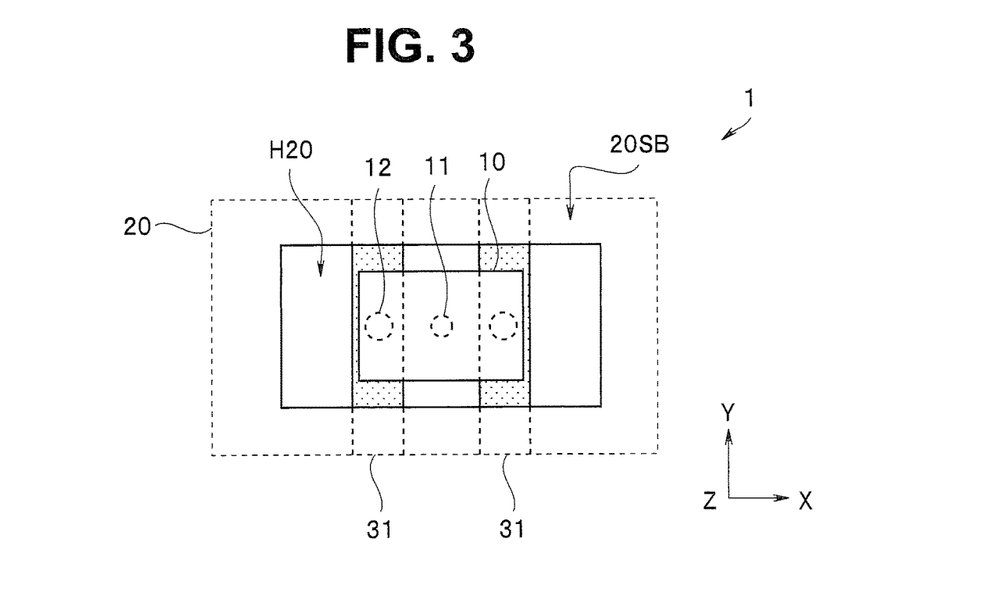
FIG. 3 is a bottom view of the optical transmitter according to the first embodiment.

Note that as shown in FIG. 2, a transparent resin 24 may fill between the optical fiber 50 and the optical device 10, or a light-blocking sealing resin 23 may cover a lower surface of the optical device 10. A bonded part between the optical device 10 and the wiring pattern 31 may be reinforced by an underfill resin.

For example, the optical device 10 is a VCSEL (vertical cavity surface emitting laser) including the light emitting portion 11 configured to output light of an optical signal. For example, an extremely small optical device 10 having a planar dimension of 250 μm×450 μm includes a light emitting portion 11 having a diameter of 25 μm, and two external electrodes 12 having a diameter of 80 μm and configured to supply drive signals to the light emitting portion 11.

For example, the upper insulating layer 21 of the wiring board 20 is a base made of polyimide and having a thickness of 25 μm, and the lower insulating layer 22 of the wiring board 20 is a flexible wiring board made of polyimide and having a thickness of 15 μm. The base of the wiring board 20 may be a ceramic substrate, a glass epoxy substrate, a glass substrate, a silicon substrate, or the like.

For example, the wiring layer 30 is made of Cu having a thickness of 18 μm. That is, the thickness of two flat plate-shaped wiring patterns 31 exposed from the opening H20 of the wiring board 20 is 18 μm. A width of the wiring pattern 31 is greater than the diameter of the external electrode 12 of the optical device 10, and is 100 μm, for example. Note that the wiring layer 30 may be covered by a metal layer having a thickness of 0.1 μm, for example.

For example, an Au bump which has a height of 15 μm and which is the external electrode 12 of the optical device 10 is ultrasonically bonded to the wiring pattern 31 of the wiring board 20. Solder paste or the like may be printed on the wiring pattern 31, and the optical device 10 may be disposed and then mounted by melting the solder by reflow or the like. In a case where the external electrode 12 is an Au/Sn bump having a height of several micrometers, the external electrode 12 may be thermal-compression bonded to the wiring pattern 31. Note that the wiring board 20 may include a processing circuit for converting an electric signal from an image pickup unit to a drive signal for the optical device 10, for example.

The through hole H40 having a columnar shape and having an inner diameter that is substantially the same as an outer diameter of the optical fiber 50 to be inserted is formed to the holding member 40 having a substantially cuboid shape. The through hole H40 may have a prism shape instead of a columnar shape, as long as the through hole H40 is capable of holding the optical fiber 50 with an inner surface of the through hole H40. A material of the holding member 40 is ceramic, Si, glass, or a metal member of SUS or the like. Note that the holding member 40 has a substantially cuboid shape, with a lower surface 40SB of 600 μm by 600 μm, but the holding member 40 may have a substantially columnar shape or a substantially conical shape, with a circular lower surface, for example. The through hole H40 may have a tapered shape with a diameter of at least one opening being greater than a diameter at a mid-portion.

The holding member 40 is fixed to the first main surface 20SA of the wiring board 20, in a state where an extended line of an optical axis O of the optical fiber 50 inserted into the through hole H40 is positioned to pass through a center of the light emitting portion 11 of the optical device 10.

For example, as shown in FIG. 2, the optical fiber 50 having a diameter of 125 μm includes a core 51 having a diameter of 50 μm and configured to transmit light, and a clad 52 covering an outer periphery of the core. The end surface 50SA of the optical fiber 50 inserted into the through hole H40 is in contact with the upper surface 31SA of the wiring pattern 31 of the wiring board 20.

A distance between the light emitting portion 11 of the optical device 10 and the end surface 50SA of the optical fiber 50 is a total of the thickness of the wiring pattern 31 (18 μm) and the height of the external electrode 12 of the optical device 10 (several to 15 μm), and is extremely short. Accordingly, the optical transmitter 1 has a high optical coupling efficiency.

With the optical transmitter 1, both ends of the wiring pattern 31 are covered and supported by the upper insulating layer 21 and the lower insulating layer 22, respectively. Accordingly, the wiring pattern 31 has a high mechanical strength, and is not easily deformed by thermal stress or the like at the time of bonding of the external electrode 12 of the optical device 10 and the lower surface 31SB of the wiring pattern 31, and thus, high productivity is achieved for the optical transmitter 1.

Note that a description is given above of the optical transmitter 1, the optical device of which is a VCSEL including the light emitting portion 11 configured to output light of an optical signal, but the same advantageous effect as the advantageous effect of the optical transmitter 1 is, of course, achieved also in a case where the optical device of the optical transmitter is, for example, a PD device including a light receiving portion to which light of an optical signal is inputted.

<Modifications of First Embodiment>

Optical transmitters 1A to 1F according to first to sixth modifications of the first embodiment are similar to the optical transmitter 1 and achieve the same advantageous effect as the advantageous effect of the optical transmitter 1, and thus, components having the same functions are denoted by same reference signs, and a repeated description is omitted.

<First Modification of First Embodiment>

Figure 4:
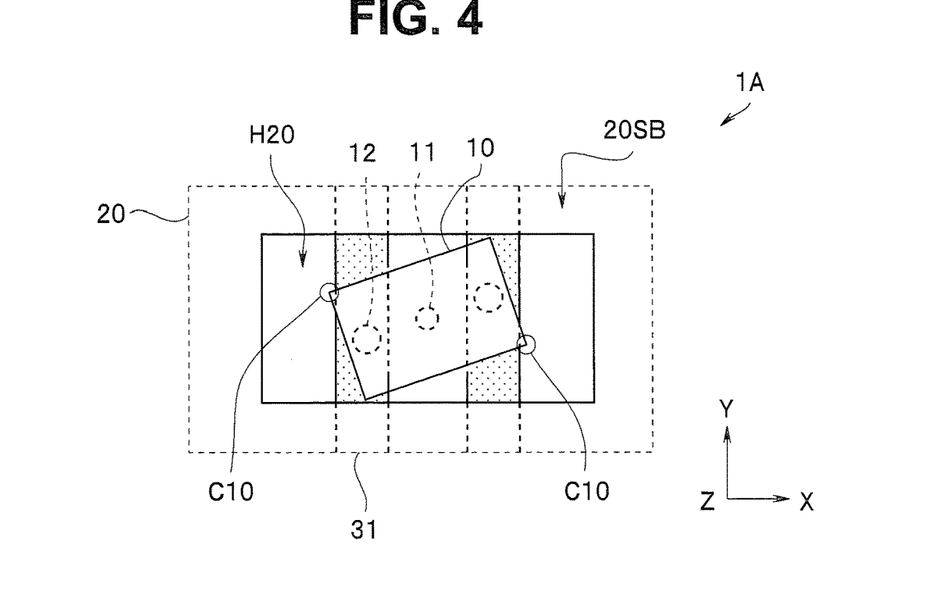
FIG. 4 is a bottom view of an optical transmitter according to a first modification of the first embodiment.

As shown in FIG. 4, with an optical transmitter 1A according to a first modification, the optical device 10 is bonded while being inclined with respect to a longitudinal direction (Y-direction) of the wiring patterns 31. In other words, the longitudinal direction of the wiring patterns 31 is inclined with respect to sides of the cuboid optical device 10, and when the wiring board 20 on which the optical device 10 is mounted is seen along an optical axis direction, such as from a top direction, or in other words, from a direction of the first main surface 20SA, that is, from above, two corner portions C10 of the cuboid optical device 10 do not overlap with the wiring patterns 31. In other words, the two corner portions C10 can be seen along the optical axis direction of the wiring board 20 where the optical device 10 is mounted.

To increase the optical coupling efficiency, a center of the through hole H40 of the holding member 40 has to be positioned immediately above the center of the light emitting portion 11 of the optical device 10. However, the light emitting portion 11 is small, and is not greatly contrasted from surroundings, and recognizing the center accurately is not easy.

The center of the light emitting portion 11 is in a predetermined relative positional relationship with the corner portions C10. For example, the center of the light emitting portion 11 is positioned at a center of a straight line connecting the two corner portions C10 which are opposing corners of the optical device 10. Accordingly, if the corner portions C10 of the optical device 10 are not overlapped with the wiring patterns 31 when seen along the optical axis direction, the center of the light emitting portion 11 can be accurately estimated based on positions of the corner portions C10.

With the optical transmitter 1A, positioning can be easily performed with high accuracy, and high productivity is achieved.

<Second Modification of First Embodiment>

Figure 5:
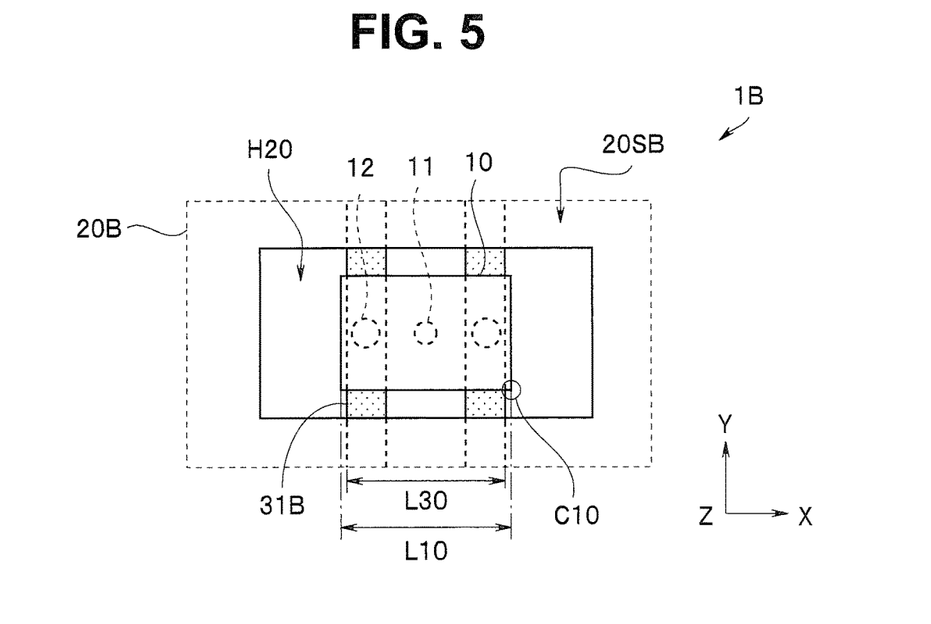
FIG. 5 is a bottom view of an optical transmitter according to a second modification of the first embodiment.

As shown in FIG. 5, with an optical transmitter 1B according to a second modification, a gap L30 between two wiring patterns 31B of a wiring board 20B is smaller than a dimension L10 of the optical device 10 in a longitudinal direction.

That is, when a wiring board 20B on which the optical device 10 is mounted is seen along the optical axis direction, four corners C10 of the cuboid optical device 10 do not overlap with the wiring patterns 31.

Accordingly, with the optical transmitter 1B, as with the optical transmitter 1A, positioning can be easily performed with high accuracy, and high productivity is achieved.

<Third Modification of First Embodiment>

Figure 6:
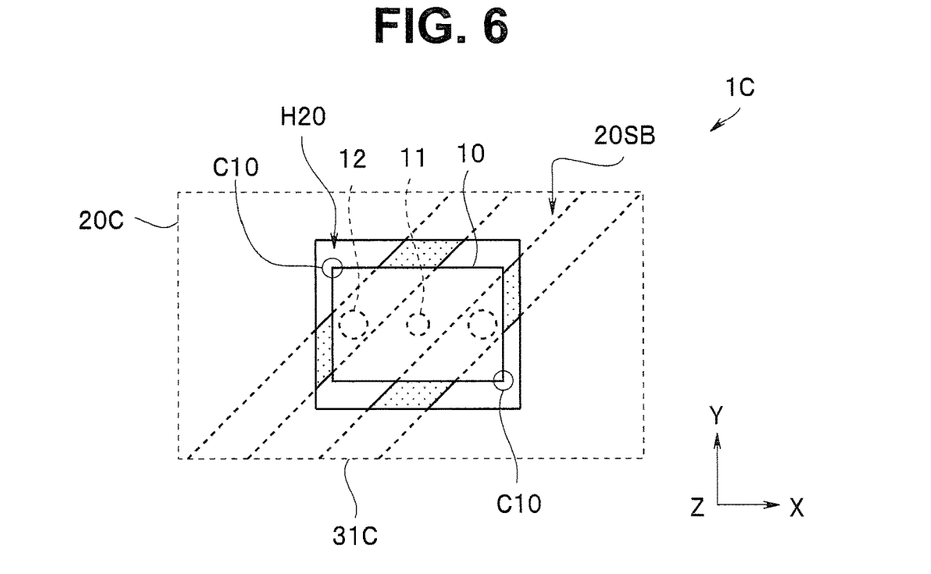
FIG. 6 is a bottom view of an optical transmitter according to a third modification of the first embodiment.

As shown in FIG. 6, with an optical transmitter 1C according to a third modification, a longitudinal direction of two wiring patterns 31C of a wiring board 20C is inclined with respect to sides of the cuboid optical device 10, and when the wiring board 20C on which the optical device 10 is mounted is seen along an optical axis, two corner portions C10 which are opposing corners of the cuboid optical device 10 are not overlapped with the wiring patterns 31C.

The wiring patterns 31C have a narrow width. However, dimensions of regions where the external electrodes 12 of the optical device 10 are bonded, that is, dimensions along an X-axis direction and a Y-axis direction, are greater than the width, and bonding is facilitated.

With the optical transmitter 1C, the width of the wiring patterns 31C is narrow, but as with the optical transmitter 1A, positioning can be easily performed with high accuracy, and high productivity is achieved.

<Fourth Modification of First Embodiment>

Figure 7:
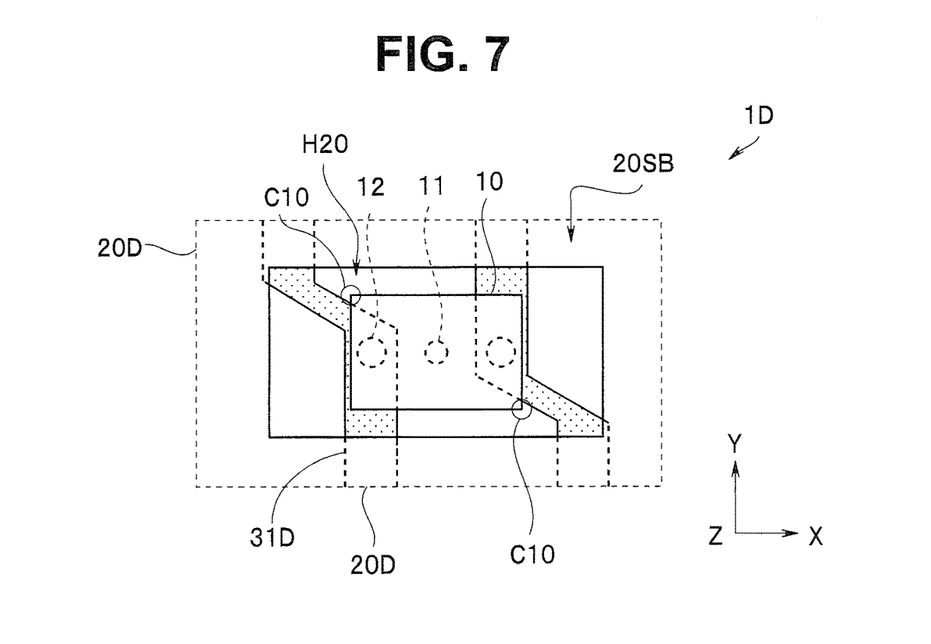
FIG. 7 is a bottom view of an optical transmitter according to a fourth modification of the first embodiment.

As shown in FIG. 7, with an optical transmitter 1D according to a fourth modification, a wiring pattern 31D includes a part, a longitudinal direction of which is orthogonal to a side of the cuboid optical device 10, and a part, the longitudinal direction of which is inclined with respect to the side. A width of the orthogonal part of the wiring pattern 31D where the external electrode 12 of the optical device 10 is bonded is 100 μm, and is wider than the inclined part. Accordingly, the optical device 10 can be easily bonded.

When a wiring board 20D on which the optical device 10 is mounted is seen from a direction of the first main surface 20SA, that is, from above, two corner portions C10 which are opposing corners of the cuboid optical device 10 are not overlapped with the wiring patterns 31D.

Accordingly, the optical transmitter 1D achieves the same advantageous effect as the advantageous effect of the optical transmitter 1C and the like, and moreover, bonding of the optical device 10 is facilitated.

<Fifth Modification of First Embodiment>

Figure 8:
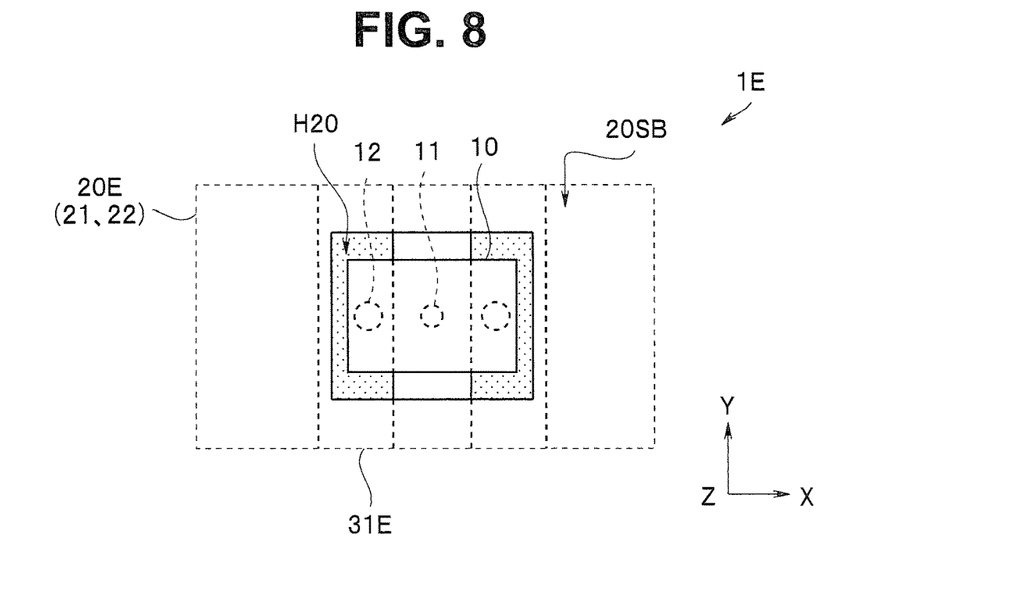
FIG. 8 is a bottom view of an optical transmitter according to a fifth modification of the first embodiment.

As shown in FIG. 8, with an optical transmitter 1E according to a fifth modification, a wiring pattern 31E is wide inside the opening H20, and is covered and supported by the upper insulating layer 21 and the lower insulating layer 22 at one side.

Accordingly, the wiring pattern 31E of the optical transmitter 1E has a higher mechanical strength than the wiring pattern 31 and the like which are supported only at both ends. With the optical transmitter 1E, deformation of the wiring pattern 31E by thermal stress or the like at the time of bonding with the external electrode 12 of the optical device 10 is small compared with the optical transmitter 1 and the like, and higher productivity is achieved.

<Sixth Modification of First Embodiment>

Figure 9:
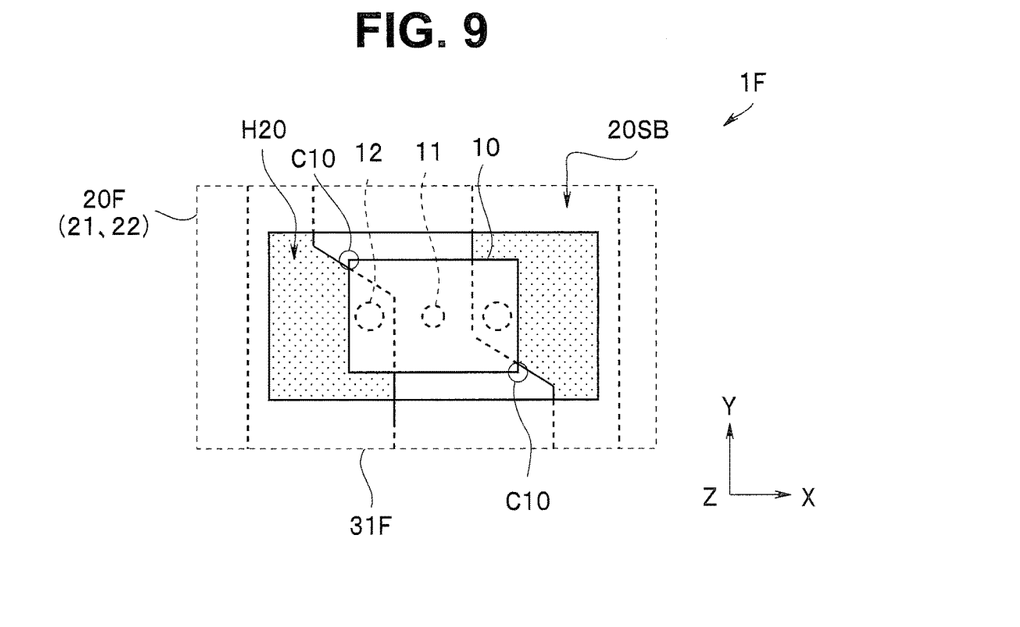
FIG. 9 is a bottom view of an optical transmitter according to a sixth modification of the first embodiment.

As shown in FIG. 9, with an optical transmitter 1F according to a sixth modification, one side of a wiring pattern 31F inside the opening H20, is covered and supported by the upper insulating layer 21 and the lower insulating layer 22. When a wiring board 20F on which the optical device 10 is mounted is seen from the direction of the first main surface 20SA, that is, from above, two corner portions C10 which are opposing corners of the cuboid optical device 10 are not overlapped with the wiring patterns 31F.

Accordingly, with the optical transmitter 1F, the wiring pattern 31F is less easily deformed at the time of bonding of the external electrode 12 of the optical device 10 and the lower surface 31SB of the wiring pattern 31F than the wiring pattern 31 and the like which are supported only at both ends.

The wiring pattern 31F includes a part, a longitudinal direction of which is orthogonal to a side of the cuboid optical device 10, and a part, the longitudinal direction of which is inclined with respect to the side. A width of the orthogonal part of the wiring pattern 31F where the external electrode 12 of the optical device 10 is bonded is wider than the inclined part. When the wiring board 20F on which the optical device 10 is mounted is seen from the direction of the first main surface 20SA, that is, from above, the two corner portions C10 of the cuboid optical device 10 are not overlapped with the wiring patterns 31F.

Accordingly, the optical transmitter 1F achieves the same advantageous effect as the advantageous effect of the optical transmitter 1E, and moreover, positioning of the holding member 40 can be easily performed.

Second Embodiment

Figure 10:
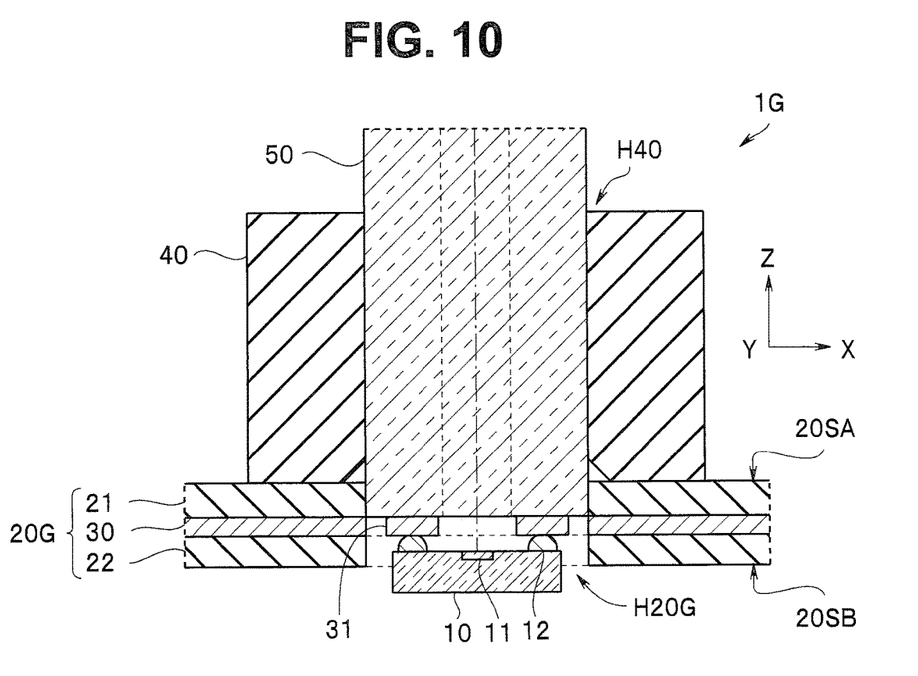
FIG. 10 is a cross-sectional view of an optical transmitter according to a second embodiment.
Figure 11:
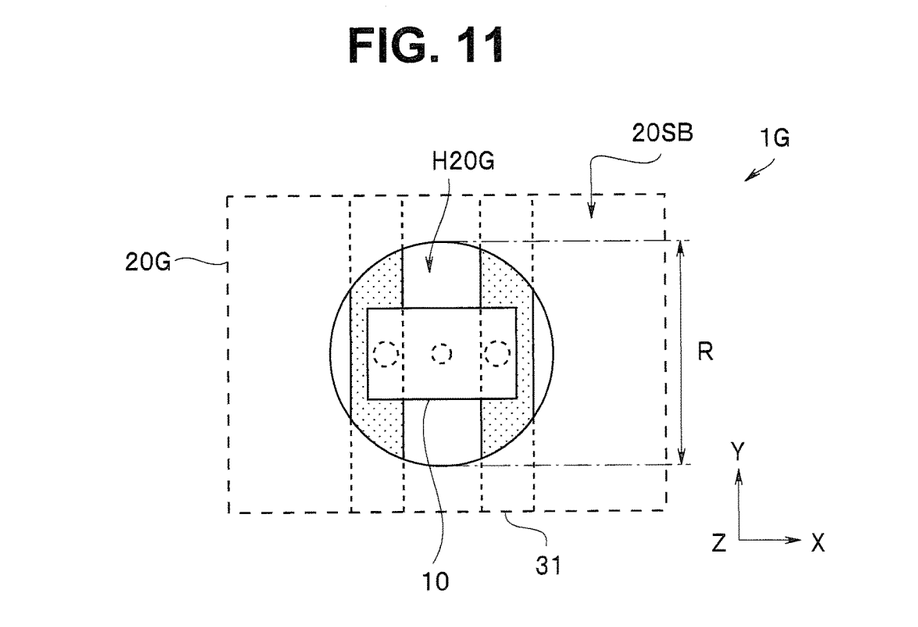
FIG. 11 is a bottom view of the optical transmitter according to the second embodiment.

An optical transmitter 1G according to a second embodiment is similar to the optical transmitter 1, and thus, components having the same functions are denoted by same reference signs, and a repeated description is omitted.

As shown in FIGS. 10 and 11, with the optical transmitter 1G, a lower part of the optical fiber 50 is fitted in an opening H20G of the upper insulating layer 21. That is, an inner diameter R of the opening H20G is substantially the same as an outer diameter of the optical fiber 50.

With the optical transmitter 1G, the holding member 40 is disposed on the first main surface 20SA of a wiring board 20G, in a state where the optical fiber 50 is inserted into the through hole H40. Then, the optical fiber 50 is fitted in the opening H20G of the upper insulating layer 21, and positioning is performed.

Accordingly, with the optical transmitter 1G, positioning of the holding member 40 can be easily performed.

<Modifications of Second Embodiment>

Figure 12:
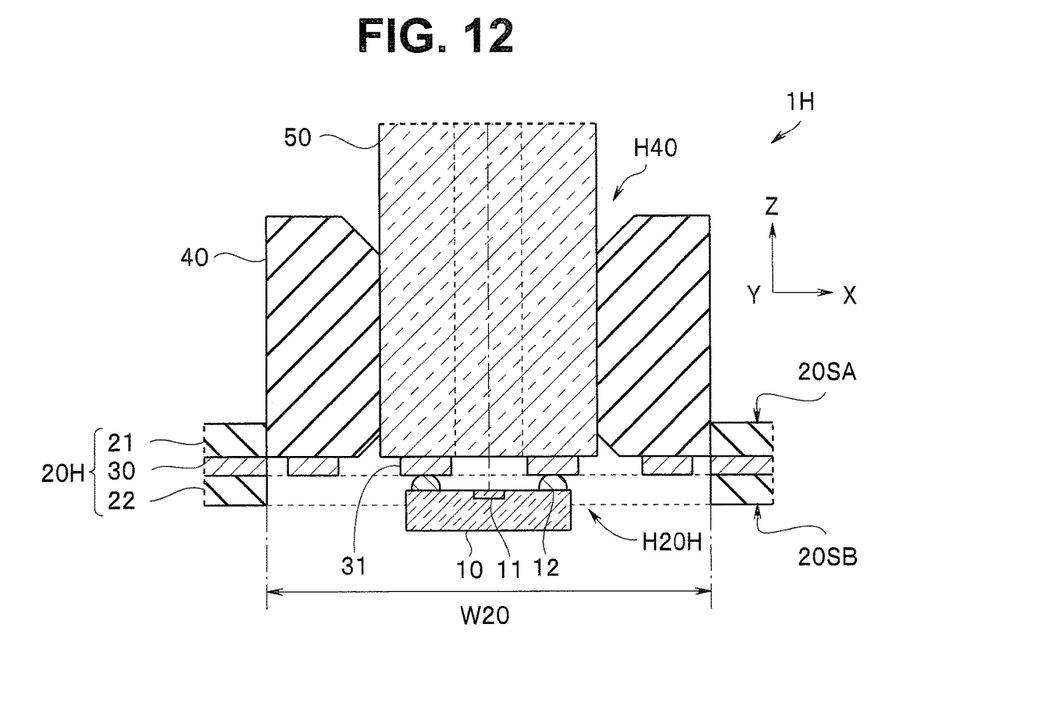
FIG. 12 is a cross-sectional view of an optical transmitter according to a first modification of the second embodiment.
Figure 13:
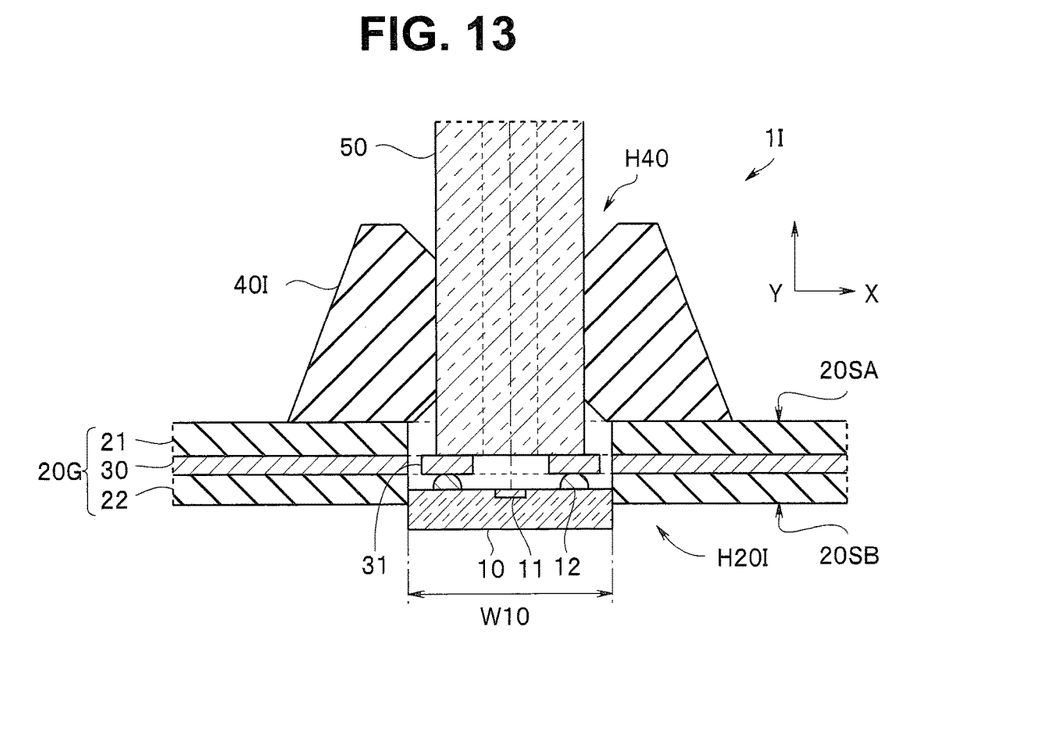
FIG. 13 is a cross-sectional view of an optical transmitter according to a second modification of the second embodiment.

Optical transmitters 1H, 1I according to first and second modifications of the second embodiment are similar to the optical transmitter 1G and achieve the same advantageous effect as the advantageous effect of the optical transmitter 1G, and thus, components having the same functions are denoted by same reference signs, and a repeated description is omitted.

<First Modification of Second Embodiment>

As shown in FIG. 12, with the optical transmitter 1H, the holding member 40 is fitted in an opening H20H of the upper insulating layer 21. If a bottom surface of the holding member 40 is circular, the opening H20H is circular, and if the bottom surface of the holding member 40 is rectangular, the opening H20H is also rectangular. An inside dimension of the opening H20H is substantially the same as an outside dimension W30 of the holding member 40.

The holding member 40 is positioned by being fitted in the opening H20H of the upper insulating layer 21.

Accordingly, with the optical transmitter 1H, positioning of the holding member 40 can be easily performed.

<Second Modification of Second Embodiment>

As shown in FIG. 13, with the optical transmitter 1I, the optical device 10 is fitted in an opening H20I of the lower insulating layer 22.

The optical device 10 is positioned by being fitted in the opening H20I of the lower insulating layer 22.

Accordingly, with the optical transmitter 1I, positioning of the optical device 10 can be easily performed.

Note that as shown in FIG. 13, a holding member 40I of the optical transmitter 1I has a substantially conical shape, with circular upper surface and lower surface. The shape of the holding member 40I may, of course, be a substantially cuboid shape, like the holding member 40 shown in FIG. 2.

Third Embodiment

An optical transmitter 1J according to a third embodiment is similar to the optical transmitter 1 and the like, and achieves the same advantageous effect as the same advantageous effect of the optical transmitter 1 and the like, and thus, components having the same functions are denoted by same reference signs, and a repeated description is omitted.

Figure 14:
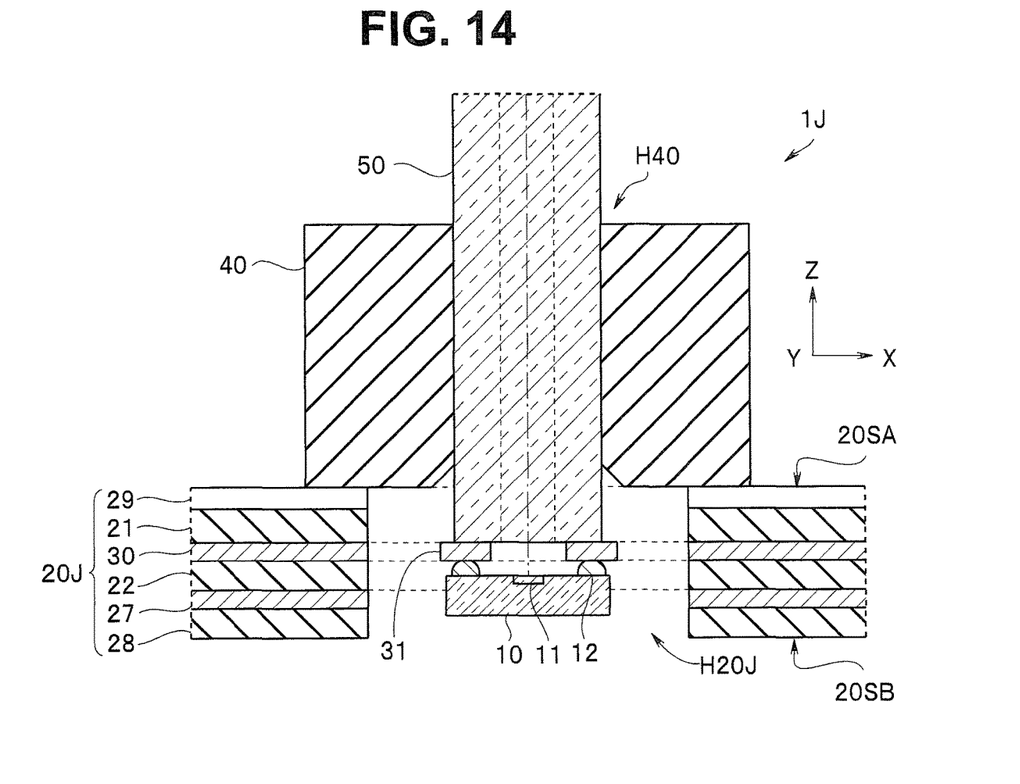
FIG. 14 is a cross-sectional view of an optical transmitter according to a third embodiment.

As shown in FIG. 14, with the optical transmitter 1J, a wiring board 20J includes a plurality of wiring layers each sandwiched between insulating layers. That is, a wiring layer 27 and an insulating layer 28 are provided below the lower insulating layer 22. Note that a solder resist layer 29 made of an insulating material is further provided above the upper insulating layer 21 of the wiring board 20J, for example.

The wiring layer 30 including the wiring pattern 31 to which the optical device 10 is bonded and with which the optical fiber 50 is in contact is an uppermost wiring layer.

With the optical transmitter 1J, the optical device 10 is housed inside an opening H20J, and a length (Z-axis dimension) is short. The optical transmitter 1J has a small height, and an outer diameter and a length of a distal end portion of an insertion portion of an endoscope can be reduced.

Fourth Embodiment

Figure 15:
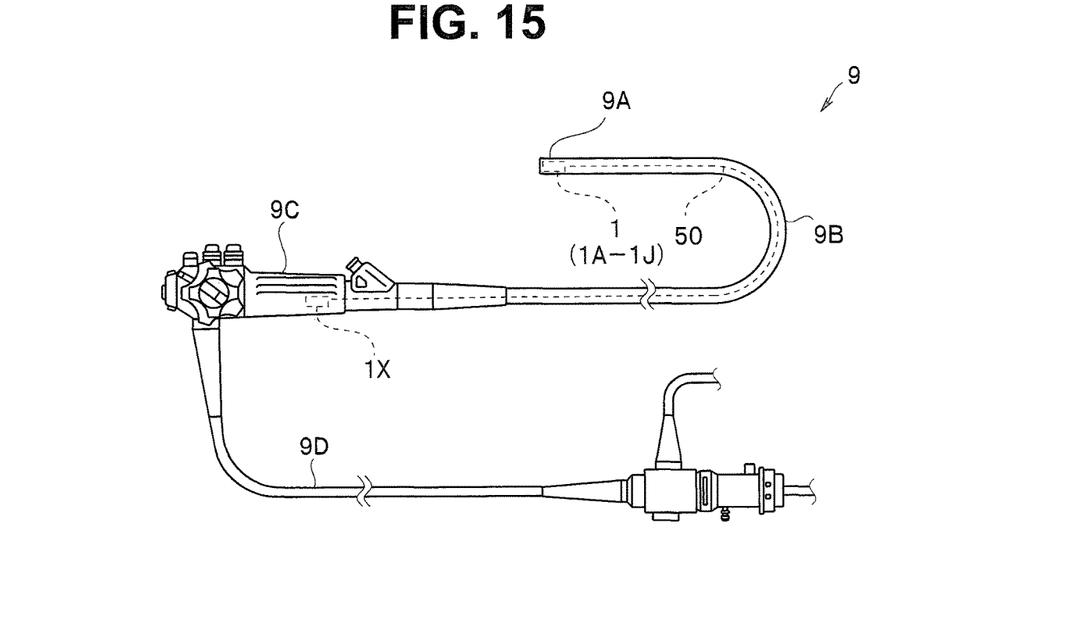
FIG. 15 is a perspective view of an endoscope according to a fourth embodiment.

Next, an endoscope 9 according to a fourth embodiment will be described. The endoscope 9 includes the optical transmitter 1 (1A, . . . , 1J) at a rigid distal end portion 9A of an insertion portion 9B.

That is, as shown in FIG. 15, the endoscope 9 includes the insertion portion 9B having an image pickup unit having an image pickup device with a large number of pixels provided at the distal end portion 9A, an operation portion 9C provided at a proximal end portion of the insertion portion 9B, and a universal cord 9D extending from the operation portion 9C.

An electric signal outputted by the image pickup unit is converted into an optical signal by the optical transmitter 1 (1A, ..., 1J), the optical device of which is a surface emitting laser, is transmitted through the optical fiber 50, is then converted again into an electric signal by an optical transmitter 1X which is provided at the operation portion 9C and an optical device of which is a PD, and is transmitted through metal wiring. That is, inside the insertion portion 9B having a small diameter, the signal is transmitted through the optical fiber 50.

As described above, the optical transmitter 1 (1A, ..., 1J) has a high optical coupling efficiency, and achieves high productivity. Accordingly, the endoscope 9 has a high optical transmission efficiency, and high productivity is achieved.

Note that the optical transmitter 1X is provided in the operation portion 9C having a relatively large installation space, but desirably has a same configuration as a configuration of the optical transmitter 1 and the like of the present invention.

The present invention is not limited to each of the embodiments described above, and various changes, combinations, and applications are possible within the scope of the invention.

What is claimed is:

1. An optical transmitter comprising:
   an optical device including a light emitting portion configured to output light of an optical signal or a light receiving portion to which light of an optical signal is inputted;
   a wiring board including a first main surface and a second main surface facing the first main surface, the optical device being mounted at a position closer to the second main surface than to the first main surface;
   a holding member fixed to the wiring board, at a position closer to the first main surface than to the second main surface, the holding member including a through hole perpendicular to the first main surface; and
   an optical fiber inserted into the through hole of the holding member, and configured to transmit the optical signal,
   wherein
   the wiring board includes a wiring pattern with a flat plate shape on a wiring layer sandwiched between an upper insulating layer and a lower insulating layer, and further includes an opening penetrating through the upper insulating layer and the lower insulating layer, and from which an upper surface and a lower surface of the wiring pattern are exposed, and
   an end surface of the optical fiber is in contact with the upper surface of the wiring pattern, and an external electrode of the optical device is bonded to the lower surface.

2. The optical transmitter according to claim 1, wherein both ends of the wiring pattern exposed inside the opening are covered and supported by the upper insulating layer and the lower insulating layer, respectively.

3. The optical transmitter according to claim 1, wherein when the wiring board on which the optical device is mounted is seen along an optical axis direction of the optical fiber, at least two corner portions of the optical device with a cuboid shape are not overlapped with the wiring pattern of the wiring board.

4. The optical transmitter according to claim 1, wherein when the wiring board on which the optical device is mounted is seen along an optical axis direction of the optical fiber, a longitudinal direction of the wiring pattern is inclined with respect to a side of the optical device with a cuboid shape.

5. The optical transmitter according to claim 1, wherein one side of the wiring pattern inside the opening is covered and supported by the upper insulating layer and the lower insulating layer.

6. The optical transmitter according to claim 1, wherein the optical device is fitted in the opening of the lower insulating layer.

7. The optical transmitter according to claim 1, wherein the optical fiber is fitted in the opening of the upper insulating layer.

8. The optical transmitter according to claim 1, wherein the holding member is fitted in the opening of the upper insulating layer.

9. The optical transmitter according to claim 1, wherein
   the wiring board includes a plurality of wiring layers each sandwiched between insulating layers, and
   the wiring layer including the wiring pattern to which the optical device is bonded and with which the optical fiber is in contact is an uppermost wiring layer.

10. An endoscope comprising the optical transmitter according to claim 1 at a rigid distal end portion of an insertion portion.

* * * * *